United States Patent [19]

Goegelman et al.

[11] Patent Number: 4,668,696

[45] Date of Patent: May 26, 1987

[54] NOVEL AVERONECTIN FERMENTATION PRODUCT OF A MICROORGANISM WITH ANTHELMINTIC ACTIVITY

[75] Inventors: Robert T. Goegelman, Linden; Raymond F. White, Englishtown; Edward S. Inamine, Rahway, all of N.J.

[73] Assignee: Merck & Co., Inc., Rahway, N.J.

[21] Appl. No.: 759,779

[22] Filed: Jul. 29, 1985

[51] Int. Cl.[4] .................... C07D 493/22; A61K 31/34
[52] U.S. Cl. ................................... 514/450; 549/264; 435/119
[58] Field of Search ......................... 549/264; 514/450

[56] References Cited

U.S. PATENT DOCUMENTS 4,199,569  4/1980  Chabala et al. ..................... 549/264
4,206,205  6/1980  Mrozik et al. ...................... 549/264
4,310,519  1/1982  Albers-Schonberg et al. .... 549/264

*Primary Examiner*—Jane T. Fan
*Attorney, Agent, or Firm*—David L. Rose; Michael C. Sudol, Jr.

[57] ABSTRACT

There is disclosed a macrolide isolated from the fermentation broth, with 22,23-dihydro avermectin Bla aglycone as a substrate, of a known microorganism identified as MA-5853. The structure of the novel compound isolated from the microorganism is presented based upon analytical studies. The compound is a highly potent antiparasitic, insecticidal, and anthelmintic agent. Compositions for such uses are also disclosed.

3 Claims, 1 Drawing Figure

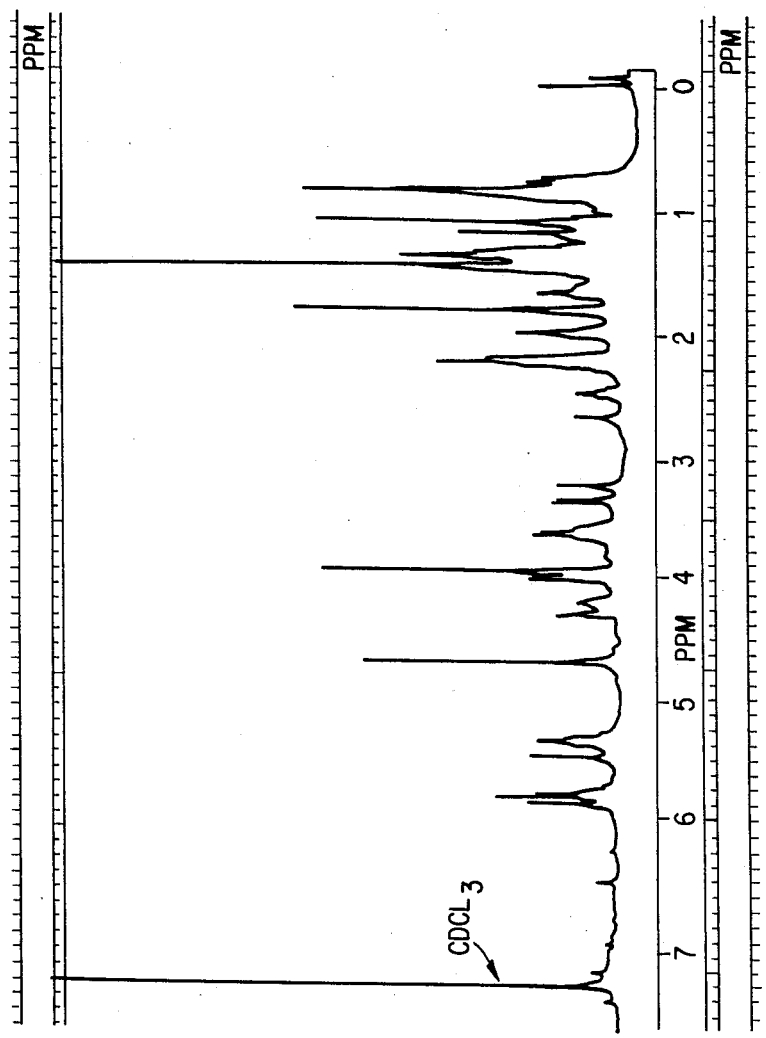

NOVEL AVERONECTIN FERMENTATION PRODUCT OF A MICROORGANISM WITH ANTHELMINTIC ACTIVITY

BACKGROUND OF THE INVENTION

The instant novel compound is related to the avermectin compounds disclosed in U.S. Pat. No. 4,310,519, dihydro avermectin compounds disclosed in U.S. Pat. No. 4,199,569 and avermectin aglycones disclosed in U.S. Pat. No. 4,206,205. However the instant compound possesses significant structural differences which readily differentiate it from the prior art compounds.

SUMMARY OF THE INVENTION

This invention is concerned with a novel chemical compound. In particular, it is concerned with a novel macrocyclic lactone which is produced by the fermentation, with 22,23-dihydro avermectin Bla aglycone as a substrate, of a nutrient medium with a strain of the microorganism Streptomyces bikiniensis MA-5853 which is a known microorganism available from the Northern Regional Research Laboratories as NRRL 2737. Thus, it is an object of this invention to provide for such novel compound, and a method for preparing such product microbiologically. It is a further object of this invention to provide for the recovery and purification of such compound from the fermentation broth. This substance has antiparasitic and insecticidal activity, in particular anthelmintic, acaracidal and nematocidal activity, and it is, thus, an additional object of this invention to provide novel anti-parasitic and insecticidal compositions containing the disclosed compound. Further objects of this invention will become apparent from the following description of this invention.

DESCRIPTION OF THE INVENTION

In accordance with this invention, a novel substance is described, which are prepared by growing under controlled conditions, a known strain of microorganism, Streptomyces bikiniensis MA-5853 with 22,23-dihydro-avermectin-Bla aglycone. The compound is obtained by fermentation and recovered in substantially pure form as described herein.

The culture designated MA-5853 is in the culture collection of Merck & Co., Inc., Rahway, N.J. A sample of this culture, capable of producing the herein described compounds, is available from the ARS Culture Collection of the Northern Regional Research Laboratories Agricultural Research Service, 1815 University Street, Peoria, Ill., 61604 and has been assigned the accession number NRRL 2737.

The instant compound is produced during the aerobic fermentation of suitable aqueous nutrient media under conditions described hereinafter, with a strain of Streptomyces bikiniensis MA-5853. Aqueous media such as those used for the production of many antibiotic substances are suitable for use in this process for the production of this macrocyclic compound. Such nutrient media contain sources of carbon and nitrogen assimilable by the microorganism and generally low levels of inorganic salts. In addition, the fermentation media may contain traces of metals necessary for the growth of the micro-organisms, and production of the desired compound. These are usually present in sufficient concentrations of the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by Streptomyces bikiniensis MA-5853 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of Streptomyces bikiniensis MA-5853.

| Medium 1 | |
|---|---|
| Dextrose | 1.0 g |
| Dextrin (Fisher) | 10.0 g |
| Beef Extract (Difco) | 3.0 g |
| Yeast Autolysate (Ardamine pH, Yeast Prod.) | 5.0 g |
| NZ Amine Type E (Sheffield) | 5.0 g |
| MgSO$_4$.7H$_2$O | 0.05 g |
| Phosphate Buffer | 2 ml |
| CaCO$_3$ | 0.5 g |
| dH$_2$O | 1000 ml |
| pH 7.0–7.2 | |
| Phosphate Buffer: | |
| KH$_2$PO$_4$ | 91.0 g |
| Na$_2$HPO$_4$ | 95.0 g |
| dH$_2$O | 1000 ml |
| pH 7.0 | |
| Medium 2 | |
| Yeast Extract (Difco) | 4.0 g |
| Malt Extract (Difco) | 10.0 g |
| Dextrose | 4.0 g |
| dH$_2$O | 1000 ml |
| Agar | 20 g |
| pH 7.2 | |
| Medium 3 Basal | |
| Sucrose | 103 g |
| K$_2$SO$_4$ | 0.25 g |
| Glucose | 10 g |
| L-Asparagine | 1.8 g |
| Casamino Acids (Difco) | 0.1 g |
| MgCl$_2$.6H$_2$O | 10.12 g |
| Trace Element Mix A | 2 ml |
| dH$_2$O | to 700 ml |
| Agar | 22.0 g |
| Post-sterilization additions, per 700 ml Basal: | |
| 100 ml of CaCl$_2$ solution (29.5 g/1000 ml dH$_2$O) | |
| 100 ml of KH$_2$PO$_4$ solution (0.5 g/1000 ml dH$_2$O) | |
| 100 ml of Tes solution (0.3 g Tris HCl + 0.1 g EDTA + | |

0.14 g NaCl in 1000 ml dH₂O, adjust to pH 8.0)
Trace Element Mix A Composition:

| | |
|---|---|
| Fe(SO₄)₃.7H₂O | 250 mg |
| MnCl₂.4H₂O | 500 mg |
| CuCl₂.2H₂O | 25 mg |
| CaCl₂.2H₂O | 1000 mg |
| H₃BO₃ | 50 mg |
| (NH₄)₆Mo₇O₂₄.4H₂O | 20 mg |
| ZnSO₄.7H₂O | 100 mg |
| Co(NO₃)₂.6H₂O | 20 mg |
| 0.1N HCl | 1000 ml |
| Medium 4 | |
| Dextrin (Fisher) | 40 g |
| Distillers Solubles (Grain Processing Corp.) | 7 g |
| Yeast Extract (Oxoid) | 5 g |
| CoCl₂.6H₂O | 50 mg |
| dH₂O | 1000 ml |
| pH 7.3 | |
| Medium 5 | |
| Dextrose | 45 g |
| Peptonized Milk (Sheffield) | 24 g |
| Ardamine pH (Yeast Products, Inc.) | 2.5 g |
| Polyglycol 2000 (Dow) | 2.5 ml |
| dH₂O | 1000 ml |
| pH 7.0 | |
| Medium 6 | |
| Dextrose | 0.1% |
| Soluble Starch (Fisher) | 1.0 |
| Beef Extract (Difco) | 0.3 |
| Yeast Autolysate (Ardamine pH Yeast Products) | 0.5 |
| NZ Amine Type E Sheffield | 0.5 |
| MgSO₄.7H₂O | 0.005 |
| KH₂PO₄ | 0.0182 |
| Na₂HPO₄ | 0.0190 |
| CaCO₃* | 0.05 |
| dH₂O | 1000 ml |
| pH 7.0–7.2 with NaOH | |

*Added after pH adjustment

The fermentation employing *Streptomyces bikiniensis* MA-5853 can be conducted at temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Streptomyces bikiniensis* MA-5853 loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces bikiniensis* MA-5853. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 500 RPM and about 2 to 20 cubic feet per minute (CFM) of air.

The separation of the novel compound from the whole fermentation broth and the recovery of said compound is carried out by solvent extraction and application of chromatographic fractionations with various chromatographic techniques and solvent systems.

The instant compound has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compounds. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, ethyl acetate, methanol, and ethanol and the like are preferred. The solvent is evaporated and the residue further chromatographed using column chromatography, thin layer chromatography, preparative layer chromatography, high pressure liquid chromatography, preferably reverse phase, and the like, with silica gel, aluminum oxide, dextran gels and the like, as the chromatographic medium, with various solvents and combinations of solvents as the eluent. Thin layer, high pressure, liquid and preparative layer chromatography may be employed to detect the presence of, and to isolate the instant compound. The use of the foregoing techniques as well as other known to those skilled in the art, will afford purified compositions containing the instant compound. The presence of the desired compound is determined by analyzing the various chromatographic fractions for biological activity against selected parasites, or physicochemical characteristics. The structure of the instant compound has been determined by detailed analysis of the various spectral characteristics of the compounds, in particular their nuclear magnetic resonance, mass, ultraviolet and infrared spectra.

Based on these experimental data, the instant compound is believed to have the following structural formula based upon the immediately preceding analytical data:

The compound is assigned the name 23-epi-24a-hydroxy-22,23-dihydro avermectin B1a aglycone.

| HR—MS | Found | Calculated | For | Assignment |
|---|---|---|---|---|
| | 618.3401 | 618.3404 | $C_{34}H_{50}O_{10}$ | $M^+$ |

The structure is as follows:

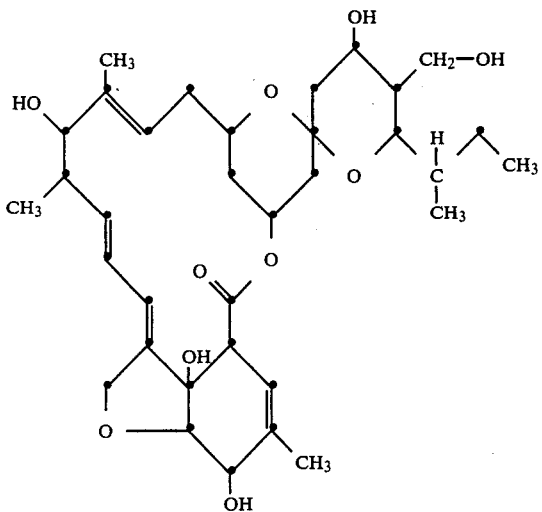

The nuclear magnetic resonance spectrum for this compound is found in the attached FIGURE and was originally recorded in $CDCl_3$ at ambient temperature on a Varian SC-300 NMR Spectrometer. Chemical shifts are shown in ppm relative to tetramethylsilane as an internal standard at zero ppm.

The novel compound of this invention has significant parasiticidal activity as an anthelmintic, insecticide and acaricide, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while other such as Dictyocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in death of the infected host. The compound of this invention has unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compound is also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compound is also of value against arthropods parasitizing man, biting insects and other dipterous pests causing annoyance to man.

The compound is also active against household pests such as the cockroach, Blatella sp., clothes moth, Tineola sp., carpet beetle, Attagenus sp. and the housefly *Musca domestica*.

The compound is also useful against insect pests of stored grains such as Tribolium sp., Tenebrio sp. and of agricultural plants such as spider mites, (tetranychus sp.), aphids (Acyrthiosiphon migratory orthopterans such as locusts and immature stages of insects living on plant tissue. The compound is useful as a nematocide for the control of soil nematodes and plant parasites such as Meloidogyne spp. which may be of importance in agriculture.

This compound may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compound in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compound of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol, formal and aqueous parenteral formulations are also used. The active compound is dissolved or suspended in the parenteral formulation for administration; such formulations generally contain from 0.005 to 5% by weight of the active compound.

Although the antiparasitic agent of this invention finds its primary use in the treatment and/or prevention of helminthiasis, it is also useful in the prevention and treatment of diseases caused by other parasites, for example, arthropod parasites such as ticks, lice, fleas, mites and other biting insects in domesticated animals and poultry. It is also effective in treatment of parasitic diseases that occur in other animals including humans. The optimum amount to be employed for best results will, of course, depend upon the species of animal to be treated and the type and severity of parasitic infection or infestation. Generally, good results are obtained with our novel compound by the oral administration of from about 0.001 to 10 mg per kg of animal body weight, such total dose being given at one time or in divided doses over a relatively short period of time such as 1-5 days. With the preferred compound of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compound described herein is administered as a component of the feed of the animals, or dissolved or suspended in the drinking water, compositions are provided in which the active compound is intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compound is intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned, the compound of this invention is usually fed at concentrations of between 0.00001 to 0.002% in the feed in order to achieve the desired antiparasitic result.

In addition, where the instant compound is to be added to an animal's feed, it is possible to utilize the dried mycelial cake from the fermentation broth. The mycelia contain a preponderance of the activity and since the level of the activity of the mycelia can be determined, it can be added directly to the animal's feed.

The compound of this invention has a broad spectrum of activity against many internal parasites at low dosage levels and in many different animals. At levels of about 2.5 mg per kg of animal body weight, concentrated mixtures of the instant compounds are fully active in sheep against *Haemonchus contortus, Ostertagia circumcincta, Trichostrongylus axei, Trichostrongylus colubriformis,* Cooperia spp., and *Oesophagostomum columbianum.* Similarly in cattle at dosages as low as 0.043 mg/kg the instant compound is fully active against *Ostertagia ostertage, Trichostrongylus axei, Trichostrongylus colubriformis, Oesophagostomum radiatum* and *Dictyocaulus viviparus.* In addition, a horse infected with bots (*Gastrophilus intestinalis* and *Gastrophilus haemorrhoidalis*), large and small strongylus and Oxyuris was successfully treated with 10 mg/kg (about 1% active compound by weight) of a mixed concentrate of the instant compounds, and a dog infected with the microfilarial stage of heartworm (*Dirofilaria immitis*) was successfully treated with a single oral dose at 10 mg/kg (about 1% active compound by weight) of a concentrate of the instant compound. In rodents, such as mice, infections of Syphacia, Nematospiroides and Aspiculuris have been successfully treated by the oral administration of the instant compound or of the concentrate obtained from the extraction of the mycelia.

The compound of this invention is also useful in combatting agricultural pests that inflict damage upon crops while they are growing or while in storage. The compound is applied using known techniques as sprays, dusts, emulsions and the like, to the growing or stored crops to effect protection from such agricultural pests.

The anthelmintic activity of the instant compound may be determined by orally administering via the feed, a sample of the individual compound, a concentrated extract, and the like to a mouse which had been infected 3 days earlier with *Nematospiroides dubius.* At 11, 12 and 13 days after the initiation of the medication, the feces of the mouse are examined for *N. dubius* eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

Transformation Methodology

| Media: | g/l |
| --- | --- |
| Seed Medium A | |
| Dextrose | 4.0 g |
| Nutrient Broth | 4.0 g |

-continued

| Media: | g/l |
|---|---|
| Yeast Extract | 4.0 g |
| Malt Extract | 10.0 g |
| 1000 ml distilled H₂O pH | 7.3 g |
| Slant Medium B | 20.0 g |
| Medium A plus Agar | |
| Transformation Medium C | 0.25 g |
| Same as Medium A, plus substrate at | |

A lyophile tube was aseptically opened and grown in seed Medium A (20 ml in a 250 ml 3-baffle Erlenmyer flask) for 48 hours on a rotary shaker (220 rpm) at 27° C.

This seed was then used to inoculate slants (Medium B), transformation flasks (Medium C), and to prepare frozen vials for future studies.

The substrate was added post sterilization and prior to inoculation. Methanol was used to solubilize the substrate for filter sterilization and addition. The transformation flasks (40 ml Medium C in 250 ml 3-baffle Erlenmyer flask) were incubated for 7 days with agitation (220 rpm) at 27° C. Following incubation, the whole broths were extracted as follows:

Extraction Methodology a. 50 ml methylene chloride were added to 40 ml whole broth and mechanically agitated for 15 minutes. The emulsion was broken by centrifugation and the methylene chloride separated. Step "a" was repeated 3 times.
b. The pooled methylene chloride extracts were taken to dryness under vacuum.
c. The dried methylene chloride fraction was solubilized with 25 ml (×3) ethanol/0.1M K₂HPO₄, pH 7.0 (40/60). Three extracts pooled.
d. The phosphate buffer: ethanol fraction was extracted with 25 ml cyclohexane (×3) to remove the residual substrate. The cyclohexane fractions were pooled and taken to dryness under vacuum. The residue was solubilized with a known volume of methanol, dried with anhydrous Na₂SO₄ and, where appropriate, total radioactivity determined by scintillation counting.
e. The phosphate buffer: ethanol fraction previously extracted with cyclohexane, was then extracted with 25 ml methylene chloride (×3) to separate the altered substrate. The methylene chloride fractions were pooled and taken to dryness under vacuum. The residue was solubilized with a known volume of methanol, dried with anhydrous Na₂SO₄ and total radioactivity determined by scintillation counting.
f. All organic fractions were submitted for HPLC analysis to determine and isolate non-substrate avermectins.

Specific Example A

Culture: *Streptomyces bikiniensis* MA5853 NRRL 2737
Substrate: 1 mg $^3$H-22,23, dihydro-avermectin-B1a aglycone
Sample: Cyclohexane Ext. (A) 2.0×10⁵ CPM Total
Sample: methylene chloride Ext. (B) 3.88×10⁶ CPM Total Specific Example B Culture: *Streptomyces bikiniensis* MA5853 NRRL 2737
Substrate: 10 mg 22,23, dihydro-avermectin-B1a aglycone
Ten flasks pooled and extracted for product isolation and identification.
Sample: Cyclohexane Ext. (C)
Sample: Methylene chloride Ext. (D)

EXAMPLE 2

The final methylene chloride extract residue, sample D from Example 1B was dissolved in 1 ml of methanol and subjected to preparative HPLC chromatography on a DuPont Zorbax ODS reverse phase C₁₈ column 2.1×25 cm, at room temperature, using a solvent system of 75/25 v/v methanol/water at a flow rate of 10 ml/minute. The effluent stream was monitored at 243 nm using an LDC Spectromonitor II at a setting of 1.28 AUFS, and a Spectra-Physics SP4100 computing integrator. Twenty-four fractions were collected. Fractions 1–3, 4.5 minutes to 7.8 minutes, were combined and concentrated to dryness and labeled Sample E. Fractions 5–7, 8.7 to 13.0 minutes were combined and concentrated to dryness and labeled Sample F.

EXAMPLE 3

Samples E and F from Example 2 were combined in 1 ml of 60/40 v/v methanol/water and subjected to preparative HPLC chromatography on a DuPont Zorbax ODS C₁₈ reverse phase column 2.1×25 cm at room temperature using a solvent system of 60/40 v/v methanol/water at a flow rate of 10 ml/min. The effluent stream was monitored at 243 nm using an LDC Spectromonitor II at a setting of 0.64 AUFS and a Spectra-Physics SP4100 computing integrator. Thirty-six fractions were collected. Fraction number seven, 24 to 33.6 minutes, was concentrated to dryness. The residue was taken up in five ml of methanol and labeled sample G. Ultra-violet quantitation of samples as 22,23-dihydro-avermectin-B$_{1a}$-aglycone calculated as follows:

$$\text{Conc} = \frac{\text{O.D. 244 nm} \times 10 \times \text{dilution}}{0.365} \times \frac{586}{875} \times \text{volume}$$

Sample G at a dilution of 1:5 in methanol $$\text{Conc} = \frac{1.586 \times 10 \times 5}{0.365} \times \frac{586}{875} \times 5 = 727 \text{ mcg}$$

EXAMPLE 4

Sample G from Example 3 was concentrated to dryness and the residue taken up in 100 mcl of methanol and subjected to HPLC chromatography on a DuPont Zorbax OD C₁₈ reverse phase column 0.46×25 cm at room temperature using a solvent system at 60/40 v/v methanol/water at a flow rate of 0.5 ml/min. The effluent stream was monitored at 243 nm using a Hewlett-Packard 1040A HPLC detection system and a Spectra-Physics SP4100 computing integrator. Twenty fractions were collected. Fractions eight thru ten, 13.2 to 18.5 minutes, were combined, concentrated to dryness and taken up in one ml of methanol for ultra-violet quantitation. Sample labeled H. Sample concentration calculated as a 22,23-dihydro-avermectin-B$_{1a}$-aglycone as follows:

$$\text{Conc} = \frac{\text{O.D. 244 nm} \times 10 \times \text{dilution}}{0.365} \times \frac{586}{875} \times \text{volume}$$

Sample H at a dilution of 1:25 in methanol $$\text{Conc} = \frac{0.798 \times 10 \times 25}{0.365} \times \frac{586}{875} \times 1 = 366 \text{ mcg}$$

Sample H was assigned to strucutre 23-epi-24a-dihydroxy-22,23-dihydro-avermectin-B1a-aglycone.

What is claimed is:

1. A compound having the formula:

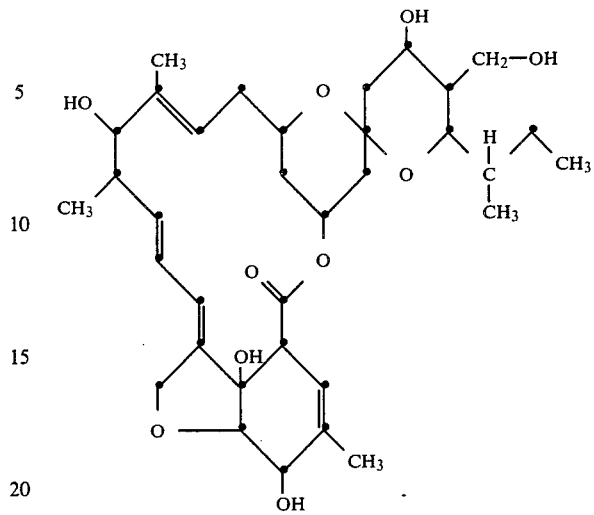

2. A method for the treating of parasitic diseases in animals which comprises administering to an animal infected with parasites, an effective amount of a compound of claim 1.

3. A composition useful for the treatment of parasitic diseases which comprises an inert carrier and an effective amount of a compound of claim 1.

* * * * *